United States Patent
Kasai et al.

(10) Patent No.: US 11,313,863 B2
(45) Date of Patent: Apr. 26, 2022

(54) MEASUREMENT OF GLYCOPROTEIN

(71) Applicant: ARKRAY, Inc., Kyoto (JP)

(72) Inventors: Takuho Kasai, Kyoto (JP); Satoshi Yonehara, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 467 days.

(21) Appl. No.: 16/148,886

(22) Filed: Oct. 1, 2018

(65) Prior Publication Data

US 2019/0137509 A1   May 9, 2019

(30) Foreign Application Priority Data

Oct. 2, 2017 (JP) .............................. JP2017-192867
Sep. 28, 2018 (JP) .............................. JP2018-185144

(51) Int. Cl.

| | | |
|---|---|---|
| *G01N 33/00* | (2006.01) | |
| *G01N 33/68* | (2006.01) | |
| *C12Q 1/26* | (2006.01) | |
| *G01N 33/72* | (2006.01) | |
| *C07K 14/47* | (2006.01) | |
| *C07K 14/76* | (2006.01) | |

(Continued)

(52) U.S. Cl.
CPC ....... *G01N 33/6839* (2013.01); *C07K 14/473* (2013.01); *C07K 14/76* (2013.01); *C07K 14/805* (2013.01); *C12Q 1/26* (2013.01); *G01N 33/533* (2013.01); *G01N 33/725* (2013.01); *G01N 2333/4728* (2013.01); *G01N 2333/805* (2013.01); *G01N 2800/042* (2013.01)

(58) Field of Classification Search
CPC .................................................. G01N 33/6839
USPC ................................................................ 436/66
See application file for complete search history.

(56) References Cited

U.S. PATENT DOCUMENTS

| | | |
|---|---|---|
| 2011/0015391 A1 | 1/2011 | Yonehara et al. |
| 2016/0123999 A1 | 5/2016 | Ogawa et al. |
| 2016/0251695 A1 | 9/2016 | Masakari et al. |

FOREIGN PATENT DOCUMENTS

| | | |
|---|---|---|
| EP | 2944699 A1 | 11/2015 |
| EP | 3061819 A1 | 8/2016 |
| JP | 3604198 B2 | 12/2004 |

(Continued)

OTHER PUBLICATIONS

WO2007072941A1—English Translation accessed from Google patents and translated by Google on Jun. 1, 2021 (Year: 2021).*

(Continued)

*Primary Examiner* — Christine T Mui
*Assistant Examiner* — Emily R. Berkeley
(74) *Attorney, Agent, or Firm* — Morgan, Lewis & Bockius LLP

(57) ABSTRACT

Abstract The disclosure provides a reagent comprising a leuco dye and a compound represented by Formula (I):

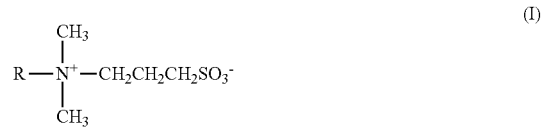

where R represents a hydrocarbon chain having 8 to 17 carbon atoms, the reagent for measuring glycoprotein, a kit comprising the reagent and a second reagent, and methods of measuring hemoglobin A1c using the reagent.

13 Claims, 2 Drawing Sheets

(51) Int. Cl.
*C07K 14/805* (2006.01)
*G01N 33/533* (2006.01)

(56) References Cited

FOREIGN PATENT DOCUMENTS

| | | |
|---|---|---|
| JP | 2013-104007 A | 11/2011 |
| JP | 5274590 B2 | 8/2013 |
| JP | 5616498 B2 | 10/2014 |
| WO | 2007/072941 A1 | 6/2007 |
| WO | 2015/005257 A1 | 1/2015 |
| WO | 2015/060429 A1 | 4/2015 |

OTHER PUBLICATIONS

Extended European Search Report issued in corresponding European Patent Application No. 18198301.6 dated Jan. 3, 2019.
Office Action issued in corresponding European Patent Application No. 18198301.6 dated Feb. 5, 2021.
Oshiro et al., "New Method for Hemoglobin Determination by Using Sodium Lauryl Sulfate (SLS)," Clin Biochem, 15:83-88 (1982).

\* cited by examiner

MEASUREMENT OF GLYCOPROTEIN

BACKGROUND OF THE INVENTION

1. Field of the Invention

The present disclosure relates to measurement of a glycoprotein, and more specifically to measurement of a glycoprotein including stabilization of a leuco dye.

2. Description of Related Art

The concentrations of glycoproteins, which are reaction products of glucose and various proteins in blood, are used as indices of a blood sugar level over the medium and long term. In particular, hemoglobin A1c (HbA1c), glycoalbumin, fructosamine, and the like are substances that are frequently measured in a clinical test, and are widely used in the diagnosis of diabetes and the monitoring of treatment conditions of diabetes. HbA1c % refers to a ratio of HbA1c, which is hemoglobin in which the N-terminus of the β-chain is glycated, to the total hemoglobin, and is used in the monitoring of a blood sugar level. In addition, HbA1c % is an important test item relating to the diagnosis of diabetes.

HbA1c % is measured using high performance liquid chromatography (HPLC), a boronate affinity method, immune nephelometry, an enzymatic method, and the like. In particular, a reagent for an enzymatic method has gained attention from the public as a methodology with which HbA1c % can be measured at the lowest cost.

An example of measurement of HbA1c % using a reagent for an enzymatic method is a method including steps (1) to (4) below.

(1) A step of denaturing hemoglobin and quantifying the denatured hemoglobin using an absorbance method.

(2) A step of hydrolyzing a glycated portion near the N-terminus of HbA1c using a protease.

(3) A step of oxidizing, using an enzyme, an oligopeptide having a glycated N-terminus produced through the hydrolysis to produce hydrogen peroxide.

(4) A step of reacting the hydrogen peroxide with a peroxidase to allow a leuco dye to produce a color and quantifying HbA1c using an absorbance method.

Leuco dyes such as DA-64 and DA-67 that are highly sensitive color forming agents are used to measure a minor component such as HbA1c. While being highly sensitive, these color forming agents also have the drawback of producing a color when exposed to oxygen, light, water, or the like. In particular, when the measurement reagent is not a dry reagent but a solution reagent, such deterioration is significant. In order to solve this problem, Japanese Patent No. 5274590, Japanese Patent No. 3604198, and JP 2013-104007A disclose a technology for stabilizing a color forming agent by adding a reductant to a color forming agent solution for the purpose of preventing the oxidation of the color forming agent. Moreover, Japanese Patent No. 5616498 discloses a technology for stabilizing a color forming agent by adding a surfactant.

SUMMARY OF THE INVENTION

In one aspect, the present disclosure provides a reagent that is suitable for measurement of a glycoprotein using an enzymatic method and contains a compound capable of stabilizing a leuco dye, and a method for measuring a glycoprotein in which the reagent is used.

In one aspect, the present disclosure relates to a reagent (also referred to as "reagent according to the present disclosure" hereinafter) for use in measurement of a glycoprotein using an enzymatic method, the reagent including a leuco dye and a compound represented by Formula (I) below:

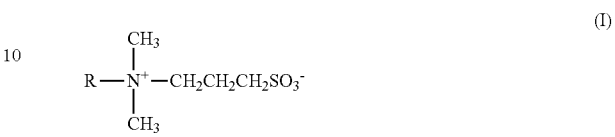

where R represents a hydrocarbon chain having 8 to 17 carbon atoms.

In another aspect, the present disclosure relates to a kit for use in the measurement of a glycoprotein using an enzymatic method, the kit including a reagent containing a peroxidase, and the reagent according to the present disclosure as a reagent separate from the reagent containing a peroxidase.

In another aspect, the present disclosure relates to a method for measuring HbA1c including (1) to (5) below, wherein the method includes mixing a sample and the reagent according to the present disclosure.

(1) Denaturing hemoglobin in the sample.

(2) Reacting glycohemoglobin in the sample with a protease to produce an N-terminal glycated peptide.

(3) Reacting the N-terminal glycated peptide with a fructosyl peptide oxidase to produce hydrogen peroxide.

(4) Reacting the produced hydrogen peroxide with a peroxidase to allow the leuco dye to produce a color.

(5) Measuring the developed color signals, and calculating a HbA1c level and a hemoglobin level.

In another aspect, the present disclosure relates to a method for measuring hemoglobin A1c including (1) to (4) below, wherein the method includes mixing a sample and the reagent according to the present disclosure.

(1) Denaturing hemoglobin in the sample.

(2) Reacting glycohemoglobin in the sample with a glycoprotein-directed fructosyl peptide oxidase to produce hydrogen peroxide.

(3) Reacting the produced hydrogen peroxide with a peroxidase to allow the leuco dye to produce a color.

(4) Measuring the developed color signals, and calculating a HbA1c level and a hemoglobin level.

With the present disclosure, the stability of a leuco dye is enhanced, thus making it possible to suppress a reduction in accuracy in measurement of a glycoprotein such as HbA1c.

DESCRIPTION OF THE INVENTION

Figure 1:
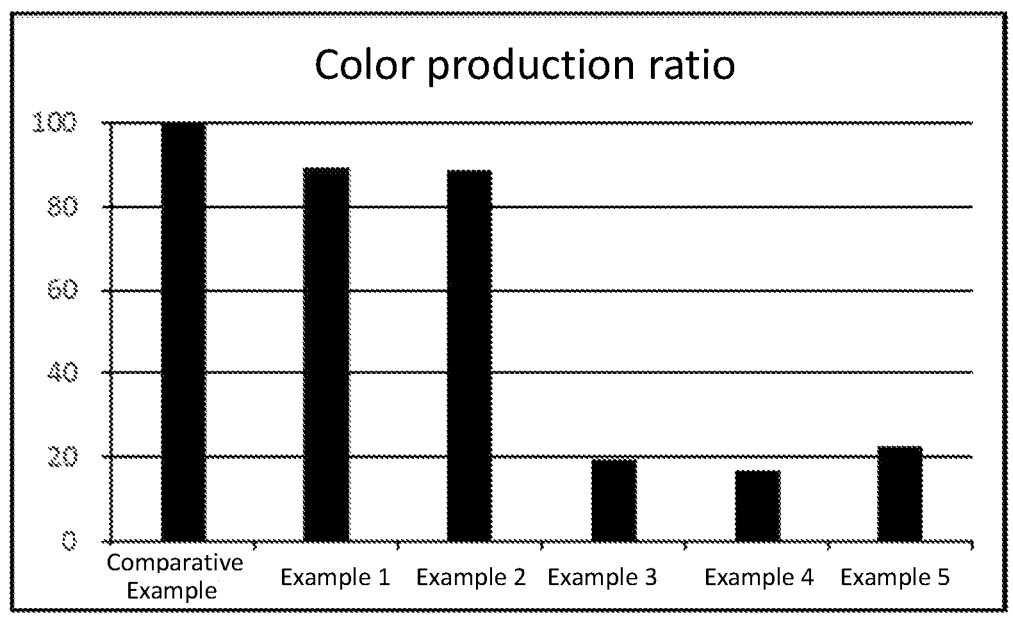
FIG. 1 is a graph showing an evaluation with respect to a suppression effect of test compounds on the natural color production of a leuco dye caused by heat treatment.

The present disclosure is based on the finding that the stability of a leuco dye used in the measurement of a glycoprotein using an enzymatic method is enhanced in the presence of a sulfobetaine including an alkyl group having a predetermined number of carbon atoms. With the present disclosure, the stability of a leuco dye in a reagent solution can be enhanced.

The "measurement of a glycoprotein" as used herein may encompass measuring a glycoprotein level in one embodiment, measuring a glycoprotein level and a protein level in another embodiment, and measuring a glycoprotein level and a protein level to determine the ratio therebetween in yet another embodiment.

Examples of the glycoprotein measured using the measurement method according to the present disclosure include fructosamine, glycoalbumin, and glycohemoglobin. In one embodiment, glycoalbumin or glycohemoglobin is measured.

The following are examples of glycohemoglobin.
HbA1c: Hb in which the N-terminus of the β-chain is glycated
GHbLys: Hb in which the amino group of Lys is glycated
GHbα: Hb in which the N-terminus of the α-chain is glycated Compound Having Ability to Stabilize Leuco Dye The reagent according to the present disclosure contains a leuco dye and a compound represented by Formula (I) below. The compound represented by Formula (I) below can stabilize a leuco dye. Accordingly, in one or more embodiments, the reagent according to the present disclosure contains the compound represented by Formula (I) below in such an amount that is effective in stabilizing the leuco dye:

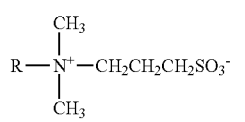

(I)

where R represents a hydrocarbon group having 8 to 17 carbon atoms.

In Formula (I), R preferably has 12 to 16 carbon atoms, and more preferably 14 carbon atoms, from the viewpoint that measurement of a glycoprotein using an enzymatic method is not inhibited and the stability of the leuco dye is enhanced. The hydrocarbon group represented by R is preferably an alkyl group, and more preferably a linear alkyl group, from the same viewpoint. R is preferably a dodecyl group or a tetradecyl group, and more preferably a tetradecyl group, from the same viewpoint.

In one or more embodiments, the content of the compound represented by Formula (I) in the reagent according to the present disclosure is preferably 0.1 g/L or more, more preferably 1 g/L or more, even more preferably 5 g/L or more, even more preferably 10 g/L or more, and even more preferably 20 g/L or more. In addition, the content of the compound represented by Formula (I) is 50 g/L or less or 40 g/L or less, for example.

Leuco Dye (Pigment)

The leuco dye in the present disclosure is preferably a highly sensitive leuco dye that can be used in trace amount detection. In one or more embodiments, examples thereof include phenothiazine-based dyes, triphenylmethane-based dyes, diphenylamine-based dyes, o-phenylenediamine, hydroxypropionic acid, diaminobenzidine, and tetramethylbenzidine. The phenothiazine-based dyes are preferable from the viewpoint that the stability of the leuco dye is enhanced.

Examples of the phenothiazine-based dyes include 10-(carboxymethylaminocarbonyl)-3,7-bis(dimethylamino)phenothiazine and salts thereof such as sodium 10-(carboxymethylaminocarbonyl)-3,7-bis(dimethylamino)phenothiazine (DA-67).

Examples of the triphenylmethane-based dyes include N,N,N',N',N'',N''-hexa(3-sulfopropyl)-4,4',4''-triaminotriphenylmethane and salts thereof such as hexasodium N,N,N',N',N'',N''-hexa(3-sulfopropyl)-4,4',4''-triaminotriphenylmethane (TPMPS).

Examples of the diphenylamine-based dyes include N-(carboxymethylaminocarbonyl)-4,4'-bis(dimethylamino)diphenylamine (DA-64).

In one or more embodiments, the content of the leuco dye in the reagent according to the present disclosure is preferably 0.005 mmol/L or more, more preferably 0.01 mmol/L or more, and even more preferably 0.03 mmol/L or more, from the viewpoint that sufficient measurement sensitivity is ensured. In addition, the content of the leuco dye is preferably 2 mmol/L or less, and more preferably 0.5 mmol/L or less, from the viewpoint that the stability of the leuco dye is enhanced.

In one or more embodiments, the ratio of the content of the compound represented by Formula (I) to the content of the leuco dye (molar ratio; the amount of substance of the compound represented by Formula (I)/the amount of substance of the leuco dye) in the reagent according to the present disclosure is preferably 5 or more, more preferably 50 or more, and even more preferably 1000 or more, from the viewpoint that a sufficient stabilizing effect is obtained. In addition, the ratio to the content of the leuco dye is preferably 10000 or less, and more preferably 5000 or less, from the viewpoint that sufficient measurement sensitivity is ensured.

The reagent according to the present disclosure may be in the form of a solution reagent or a dry reagent. In the case of the solution reagent, in one or more embodiments, the pH of the reagent according to the present disclosure is preferably 5 or more, and more preferably 6 or more. In one or more embodiments, the pH of the reagent according to the present disclosure is preferably 9 or less, and more preferably 8 or less. It should be noted that the pH is measured at a temperature of 25° C. using a pH meter.

With the reagent according to the present disclosure, in one or more embodiments, the length of preservation time of the reagent can be extended. In one or more other embodiments, reducing the change in sensitivity makes it possible to reduce the number of calibrations. In one or more yet other embodiments, the reagent can be preserved at a high temperature (e.g., 2 to 50° C.).

With the measurement of a glycoprotein using the reagent according to the present disclosure, in one or more embodiments, the calculating the glycoprotein level such as the HbA1c level and the protein level such as the hemoglobin level from the developed color signal of the leuco dye may be performed by a known method.

Embodiment A

In non-limiting Embodiment A, the reagent according to the present disclosure may be used as a reagent to be mixed with a sample in a method for measuring HbA1c including (1) to (5) below.

(1) Denaturing hemoglobin in the sample.
(2) Reacting glycohemoglobin in the sample with a protease to produce an N-terminal glycated peptide.
(3) Reacting the N-terminal glycated peptide with a fructosyl peptide oxidase (FPOX) to produce hydrogen peroxide.
(4) Reacting the produced hydrogen peroxide with a peroxidase (POD) to allow the leuco dye to produce a color.
(5) Measuring and the developed color signals, and calculating a HbA1c level and a hemoglobin level.

It should be noted that the term "mixing the reagent and a sample" and "mixing the reagent with a sample" as used herein encompasses adding the reagent to a sample, and adding a sample to the reagent.

In one or more embodiments of Embodiment A, the reagent according to the present disclosure is mixed with a sample in order to supply at least a leuco dye to be used in (4) above. That is, the leuco dye contained in the reagent according to the present disclosure is used as the leuco dye in the method for measuring HbA1c including (1) to (5) above. In one or more other embodiments of Embodiment A, the reagent according to the present disclosure is mixed with a sample in order to allow at least the leuco dye to produce a color in (4) above.

When Embodiment A is performed using a two-reagent system, two reagents, namely a first reagent and a second reagent, are added to a sample in this order or are mixed with a sample. In one or more non-limiting embodiments, the denaturation of hemoglobin in (1) above is performed by adding the first reagent to a sample or mixing the first reagent with a sample, and an absorbance measurement for measuring a hemoglobin level is performed after the first reagent is added or mixed and before the second reagent is added or mixed. Depending on the composition of the first reagent, (1) and (2) above are carried out by adding the first reagent to a sample or mixing the first reagent with a sample, and all of (1) to (4) can progress due to the second reagent being added or mixed. Therefore, the absorbance measurement for measuring a HbA1c level is performed immediately before or after the second reagent is added or mixed, and after a predetermined time period has elapsed since the second reagent is added or mixed. A HbA1c level is calculated based on the change in the value of the absorbance.

In one or more non-limiting embodiments, the reagent according to the present disclosure may be used as a second reagent in configurations A1 and A2 below and a first reagent in configurations A3 and A4 below. However, the reagent according to the present disclosure is not limited to those of the embodiments. The first reagent and second reagent may also further contain another component (e.g., additional buffer, denaturant, or leuco dye stabilizer).

Configuration A1
First reagent: FPOX, POD, denaturant, buffer
Second reagent: protease, compound represented by Formula (I), leuco dye, buffer
Configuration A2
First reagent: protease, POD, denaturant, buffer
Second reagent: FPOX, compound represented by Formula (I), leuco dye, buffer
Configuration A3
First reagent: FPOX, compound represented by Formula (I), leuco dye, buffer
Second reagent: protease, POD, buffer Configuration A4
First reagent: protease, compound represented by Formula (I), leuco dye, buffer
Second reagent: FPOX, POD, buffer Therefore, the reagent according to the present disclosure may further contain at least one of a buffer, a protease, and FPOX.

A buffer whose pH can be adjusted to near a neutral pH and that does not impair the reaction system can be used as the buffer of Embodiment A. Non-limiting examples of the buffer include N,N-bis(2-hydroxyethyl)-2-aminoethanesulfonic acid (BES), 3-morpholinopropanesulfonic acid (MOPS), N-tris(hydroxymethyl)methyl-2-aminoethanesulfonic acid (TES), 2-[4-(2-hydroxyethyl)-1-piperazinyl] ethanesulfonic acid (HEPES), N-[tris(hydroxymethyl) methyl]glycine (TRICINE), piperazine-1,4-bis(2-ethanesulfonic acid) (PIPES), piperazine-1,4-bis(2-hydroxy-3-propanesulfonic acid)dehydrate (POPSO), carbonic acid, phosphoric acid, boric acid, glycine, alanine, leucine, arginine, lysine, histidine, taurine, aspartic acid, asparagine, hydroxyproline, proline, threonine, serine, glutamic acid, glutamine, valine, cysteine, methionine, isoleucine, leucine, tyrosine, phenylalanine, ornithine, tryptophan, trishydroxymethylaminomethane, dimethylaminoethanol, triethanolamine, diethanolamine, monoethanolamine, N-methylaminoethanol, creatinine, imidazol, barbital, ammonia, ethylamine, diethylamine, and triethylamine.

As the protease of Embodiment A, a protease that is active at near a neutral pH and can react with glycohemoglobin to produce an N-terminal glycated peptide (including a glycoamino acid in the present disclosure) can be used. There is no particular limitation on the species from which the protease is derived and the enzyme family. Non-limiting examples of the protease include a serine protease, a threonine protease, a glutamic protease, an aspartic protease, and a metalloprotease. An exoprotease is preferable to an endoprotease.

As the FPOX of Embodiment, an FPOX that uses an N-terminal glycated peptide (including a glycoamino acid) as a substrate and produces hydrogen peroxide, which is a detectable intermediate product, can be used. There is no particular limitation on the species from which the FPOX is derived. An FPOX called amadoriase or fructosyl amino acid oxidase can also be used, and may be encompassed in the FPOX in the present disclosure.

As the POD of Embodiment A, a POD that can react with hydrogen peroxide and allow the leuco dye serving as a color forming substrate to produce a color can be used. There is no particular limitation on the species from which the POD is derived. A non-limiting example of the POD is a horseradish peroxidase.

A denaturant that can denature hemoglobin and does not significantly impair the activity of an enzyme contained in the first reagent can be used as the denaturant of Embodiment A. Non-limiting examples of the denaturant include denaturants (1) to (8) below. It should be noted that denaturants (1) to (7) may be used in combination with a nitrite.

(1) 3-Lauryldimethylaminobutyric acid
(2) 3-Myristyldimethylaminobutyric acid
(3) Lauryldimethylaminopropanesulfonic acid
(4) Myristyldimethylaminopropanesulfonic acid
(5) Laurylamidepropyldimethylaminobutyric acid
(6) Myristamidepropyl betaine
(7) n-Dodecyl-βD-maltoside
(8) WST-3

Alternatively, the denaturant of Embodiment A may also be the compound represented by Formula (I) instead of denaturants (1) to (8) above. The compound represented by Formula (I) can denature hemoglobin and promote a protease reaction.

A sample containing hemoglobin and glycohemoglobin can be used as a measurement sample of Embodiment A. In one or more non-limiting embodiments, examples of the measurement sample include samples containing erythrocytes, such as whole blood and hemocytes, and samples obtained by subjecting such samples to hemolysis. When the measurement sample contains erythrocytes, the sample may be hemolyzed using the first reagent or a means other than the first reagent to produce a hemolyzed sample. Erythrocytes can be hemolyzed using the existing methods. Examples of the hemolysis methods include a method employing osmotic pressure (e.g., water), a method employing a surfactant, a freezing method, and a method employing ultrasonic waves.

In one or more other embodiments, the developed color signal of the present disclosure includes absorbance, reflectance, or transmittance.

In one or more embodiments, the calculation of the HbA1c level may include converting the developed color signal into the HbA1c level using predetermined conversion factor. The conversion of the developed color signal into the HbA1c level using the predetermined conversion factor may be performed by converting the developed color signal, such as absorbance, obtained by the measurement of HbA1c, into HbA1c level on the basis of one of the conversion rules (i) to (iv) below, in one or more embodiments. The conversion rules (iv) may be performed in combination with one or more the conversion rules (i) to (iii), in one or more embodiments.

(i) Creating a calibration curve by using a known calibrating substance in the sample, and converting absorbance derived from HbA1c into the HbA1c level by using the calibration curve;

(ii) Creating a calibration curve of the leuco dye as a calibrator (calibration standard), and converting absorbance of the leuco dye into the HbA1c level by using the calibration curve of the leuco dye;

(iii) Calculating a ratio of absorbance obtained at different wavelengths, and converting the ratio into HbA1c level by using a calibration curve of the absorbance ratio;

(iv) Calculating the amount of change in the absorbance by subtracting absorbance a from absorbance b and converting the amount of change in the absorbance into the HbA1c level by using the calibration curve for the amount of change in absorbance.

the absorbance a: absorbance immediately after mixing of the sample and the reagent the absorbance b: absorbance after a lapse of a predetermined time from the mixing of the sample and the reagent The known calibrating substance, in one or more embodiments, may include calibration standards containing known amounts of HbA1c. The calibration standard, in one or a plurality of embodiments, may include frozen whole blood or blood cells, Hb solution containing HbA1c obtained by purified them, or substance containing buffer solutions and/or stabilization of Hb agents and the like therein. The known calibrating substance, in one or more embodiments, may include a primary standard substance or a regular reference substance provided by a public institution, a proofreading substance attached to a kit, and the like.

In one or more embodiments of immediately after mixing, it may be about 5 seconds to 30 seconds after mixing of the sample and the reagent. In one or more embodiments of after a lapse of a predetermined time, it may be about 1 minute to 3 minutes after mixing of the sample and the reagent.

With the calculation of the HbA1c level, in one or more embodiments, even in a case where the developed color signal is the reflectance and the transmittance can be performed.

Embodiment B

In non-limiting Embodiment B, the reagent according to the present disclosure may be used as a reagent to be mixed with a sample in a method for measuring HbA1c including (1) to (4) below.

(1) Denaturing hemoglobin in the sample.

(2) Reacting glycohemoglobin in the sample with a glycoprotein-directed fructosyl peptide oxidase (direct FPOX) to produce hydrogen peroxide.

(3) Reacting the produced hydrogen peroxide with a peroxidase to allow the leuco dye to produce a color.

(4) Measuring the developed color signals and calculating a HbA1c level and a hemoglobin level.

In one or more embodiments of Embodiment B, the reagent according to the present disclosure is mixed with a sample in order to supply at least a leuco dye to be used in (3) above. That is, the leuco dye contained in the reagent according to the present disclosure is used as the leuco dye in the method for measuring HbA1c including (1) to (4) above. In one or more other embodiments of Embodiment B, the reagent according to the present disclosure is mixed with a sample in order to allow at least the leuco dye to produce a color in (3) above.

In Embodiment B, the FPOX in Embodiment A is changed to the direct FPOX and the protease thus becomes unnecessary in the reaction system.

In one or more non-limiting embodiments, the reagent according to the present disclosure may be used as a second reagent in configurations B1 and B2 below and a first reagent in configurations B3 and B4 below. However, the reagent according to the present disclosure is not limited to those of the embodiments. The first reagent and second reagent may also further contain another component.

Configuration B1
First reagent: POD, denaturant, buffer
Second reagent: direct FPOX, compound represented by Formula (I), leuco dye, buffer
Configuration B2
First reagent: direct FPOX, denaturant, buffer
Second reagent: POD, compound represented by Formula (I), leuco dye, buffer
Configuration B3
First reagent: POD, compound represented by Formula (I), leuco dye, denaturant, buffer
Second reagent: direct FPOX, buffer
Configuration B4
First reagent: direct FPOX, compound represented by Formula (I), leuco dye, denaturant, buffer
Second reagent: POD, buffer In the case of configuration B1, in one or more non-limiting embodiments, the denaturation of hemoglobin in (1) above is carried out by adding the first reagent to a sample or mixing with a sample, and an absorbance measurement for measuring a hemoglobin level is performed after the first reagent is added (or mixed) and before the second reagent is added (or mixed). (2) and (3) can progress due to the second reagent being added or mixed. Therefore, the absorbance measurement for measuring a HbA1c level is performed immediately before or after the second reagent is added or mixed, and after a predetermined time period elapses since the second reagent is added or mixed. A HbA1c level is calculated based on the change in the value of the absorbance.

Therefore, the reagent according to the present disclosure may further contain a glycoprotein-directed fructosyl peptide oxidase (direct FPOX).

The buffer, protease, POD, denaturant, measurement sample, developed color signal, and calculation method of HbA1c of Embodiment B are the same as those of Embodiment A.

The direct FPOX of Embodiment B is an improved FPOX that has a substrate specificity to glycohemoglobin (i.e., acts directly on glycohemoglobin) (WO 2015-005257 and WO 2015-060429).

Kit

In another aspect, the present disclosure relates to a kit for use in the measurement of a glycoprotein using an enzymatic method, the kit including a reagent containing a peroxidase, and a reagent according to the present disclosure as a reagent separate from the reagent containing a peroxidase.

The kit according to the present disclosure may be a two-reagent system kit or a three-reagent system kit for measuring a glycoprotein using an enzymatic method. The two-reagent system kit is configured of two kinds of reagents, and the three-reagent system kit is configured of three kinds of reagents. In one or more non-limiting embodiments, examples of the configuration of the two-reagent system kit include configurations A1 to A4 and B1 above.

Measurement Method

In another aspect, the present disclosure relates to a method for measuring HbA1c including (1) to (5) below, wherein the method includes mixing the reagent according to the present disclosure and a sample, in order to supply at least a leuco dye to be used in (4) below.

(1) Denaturing hemoglobin in a sample.

(2) Reacting glycohemoglobin in the sample with a protease to produce an N-terminal glycated peptide.

(3) Reacting the N-terminal glycated peptide with a FPOX to produce hydrogen peroxide.

(4) Reacting the produced hydrogen peroxide with a POD to allow the leuco dye to produce a color.

(5) Measuring the developed color signals and calculating a HbA1c level and a hemoglobin level.

In another aspect, the present disclosure relates to a method for measuring HbA1c including (1) to (4) below, wherein the method includes mixing the reagent according to the present disclosure and a sample, in order to supply at least a leuco dye to be used in (3) below.

(1) Denaturing hemoglobin in a sample.

(2) Reacting glycohemoglobin in the sample with a direct FPOX to produce hydrogen peroxide.

(3) Reacting the produced hydrogen peroxide with a peroxidase to allow the leuco dye to produce a color.

(4) Measuring the developed color signals and calculating a HbA1c level and a hemoglobin level.

The measurement method according to the present disclosure is as described in Embodiments A and B above.

The present disclosure further relates to the following one or more non-limiting embodiments.

[1] A reagent for use in measurement of a glycoprotein using an enzymatic method, including
a leuco dye; and
a compound represented by Formula (I):

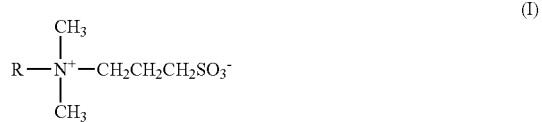

where R represents a hydrocarbon chain having 8 to 17 carbon atoms.

[2] The reagent according to [1], wherein the glycoprotein is glycohemoglobin or glycoalbumin.

[3] The reagent according to [1] or [2], wherein the glycoprotein is hemoglobin A1c.

[4] The reagent according to any one of [1] to [3], wherein the compound represented by Formula (I) is included as at least an agent for stabilizing the leuco dye.

[5] The reagent according to any one of [1] to [4], wherein the leuco dye is 10-(carboxymethylaminocarbonyl)-3,7-bis(dimethylamino)phenothiazine, N,N,N',N',N'',N''-hexa(3-sulfopropyl)-4,4',4''-triaminotriphenylmethane, N-(carboxymethylaminocarbonyl)-4,4'-bis(dimethylamino) diphenylamine, or a salt thereof.

[6] A kit for use in measurement of a glycoprotein using an enzymatic method, including:
a reagent containing a peroxidase; and
the reagent according to any one of [1] to [5] as a reagent separate from the reagent containing a peroxidase.

[7] A method for measuring hemoglobin A1c including (1) to (5) below,
wherein a sample and the reagent according to any one of [1] to [5] are mixed together:

(1) denaturing hemoglobin in the sample;

(2) reacting glycohemoglobin in the sample with a protease to produce an N-terminal glycated peptide;

(3) reacting the N-terminal glycated peptide with a fructosyl peptide oxidase to produce hydrogen peroxide;

(4) reacting the produced hydrogen peroxide with a peroxidase to allow the leuco dye to produce a color; and (5) measuring the absorbances, and calculating a hemoglobin A1c level and a hemoglobin level.

[8] A method for measuring hemoglobin A1c including (1) to (4) below,
wherein a sample and the reagent according to any one of [1] to [5] are mixed together:

(1) denaturing hemoglobin in the sample;

(2) reacting glycohemoglobin in the sample with a glycoprotein-directed fructosyl peptide oxidase to produce hydrogen peroxide;

(3) reacting the produced hydrogen peroxide with a peroxidase to allow the leuco dye to produce a color; and (4) measuring the absorbances, and calculating a hemoglobin A1c level and a hemoglobin level.

EXAMPLES

The following compounds were used in the examples, which will be described below.

Octylsulfobetaine (sulfobetaine C8):
N-octyl-N,N-dimethyl-3-ammonio-1-propanesulfonic acid (manufactured by Tokyo Chemical Industry Co., Ltd.)
Decylsulfobetaine (sulfobetaine C10):

N-decyl-N,N-dimethyl-3-ammonio-1-propanesulfonic acid (manufactured by Tokyo Chemical Industry Co., Ltd.)

Laurylsulfobetaine (sulfobetaine C12): N-dodecyl-N,N-dimethyl-3-ammonio-1-propanesulfonic acid (manufactured by Tokyo Chemical Industry Co., Ltd.)

Tetradecylsulfobetaine (sulfobetaine C14): N-tetradecyl-N,N-dimethyl-3-ammonio-1-propanesulfonic acid (manufactured by Tokyo Chemical Industry Co., Ltd.)

Hexadecylsulfobetaine (sulfobetaine C16): N-hexadecyl-N,N-dimethyl-3-ammonio-1-propanesulfonic acid (manufactured by Tokyo Chemical Industry Co., Ltd.)

Octadecylsulfobetaine (sulfobetaine C18): N-octadecyl-N,N-dimethyl-3-ammonio-1-propanesulfonic acid (manufactured by Tokyo Chemical Industry Co., Ltd.)

DA-67 (leuco dye): sodium 10-(carboxymethylaminocarbonyl)-3,7-bis(dimethylamino) phenothiazine (manufactured by Tokyo Chemical Industry Co., Ltd.)

Evaluation of Stabilization of Leuco Dye 1

This experiment was performed in order to determine a sulfobetaine that contributes to the stabilization of a leuco dye. A leuco dye (DA-67) was dissolved in a 100 mmol/L Tris-PIPES buffer (pH 6.8) such that the concentration of the leuco dye was 0.045 mmol/L. To 20 mL of this solution, each of the stabilizers shown in Table 1 was added, and a reagent was thus prepared. The prepared reagent was heated at 25° C. for 24 hours. Thereafter, a biochemical autoanalyzer (JCA-BM-6010, manufactured by JEOL Ltd.) was used with the following parameters to measure the color production amount of the reagent using purified water as a specimen. The color production amount of the reagent prior to the heat treatment performed at 25° C. for 24 hours was also measured in the same manner. Then, the difference between the color production amounts before and after the heat treatment was determined from the magnitude of the absorbance change caused by the heat treatment, and the ability to stabilize the leuco dye was evaluated. Table 1 and FIG. 1 show the results.

<First Reagent>
PIPES buffer (pH 6.4)

<Second Reagent>
Protease (product name: NEP-209; manufactured by TOYOBO Co., Ltd.): 2 U/mL
DA-67: 45 µmol/L
Sulfobetaine shown in Table 1: 1 g/L
PIPES buffer (pH 6.8)

The following are the measurement parameters used to evaluate the color production amounts of the reagents.

Main measurement wavelength: 658 nm
Complementary measurement wavelength: 694 nm
Specimen (purified water) dispensing amount: 8 µL
First reagent dispensing amount: 96 µL
Second reagent dispensing amount: 24 µL
First photometric point: 17 to 19
Second photometric point: 21

TABLE 1

|  | Stabilizer 1 g/L | Before treatment | After treatment | Difference | Color production ratio |
|---|---|---|---|---|---|
| Comp. Ex. 1 | None | 0.007 | 0.025 | 0.017 | 100 |
| Ex. 1 | Sulfobetaine C8 | 0.008 | 0.024 | 0.016 | 89 |
| Ex. 2 | Sulfobetaine C10 | 0.008 | 0.023 | 0.015 | 89 |
| Ex. 3 | Sulfobetaine C12 | 0.004 | 0.007 | 0.003 | 19 |
| Ex. 4 | Sulfobetaine C14 | 0.004 | 0.007 | 0.003 | 17 |
| Ex. 5 | Sulfobetaine C16 | 0.003 | 0.007 | 0.004 | 22 |

As shown in FIG. 1 and Table 1, the color production ratios in Examples 1 to 5 were smaller than those in Comparative Example 1. In particular, the color production ratios in Examples 3 to 5 were significantly smaller.

Evaluation of Stabilization of Leuco Dye 2

This experiment was performed in order to confirm that the stability of a leuco dye was enhanced in a sulfobetaine concentration dependent manner. A leuco dye (DA-67) was dissolved in a 100 mmol/L Tris-PIPES buffer (pH 6.8) such that the concentration of the leuco dye was 0.045 mmol/L. To 5 mL of this solution, each of the stabilizers shown in Table 2 was added, and a reagent was thus prepared. The prepared reagent was heated at 25° C. for 24 hours. Thereafter, a biochemical autoanalyzer (JCA-BM-6010, manufactured by JEOL Ltd.) was used with the following parameters to measure the color production amount of the reagent using purified water as a specimen. The color production amount of the reagent prior to the heat treatment performed at 25° C. for 24 hours was also measured in the same manner. Then, the difference between the color production amounts before and after the heat treatment was determined from the magnitude of the absorbance change caused by the heat treatment, and the ability to stabilize the leuco dye was evaluated. Table 2 and FIG. 2 show the results.

The following are the measurement parameters used to evaluate the color production amounts of the reagents.

Main measurement wavelength: 658 nm
Complementary measurement wavelength: 694 nm
Specimen (purified water) dispensing amount: 8 µL
First reagent dispensing amount: 96 µL
Second reagent dispensing amount: 24 µL
First photometric point: 17 to 19
Second photometric point: 21

Figure 2:
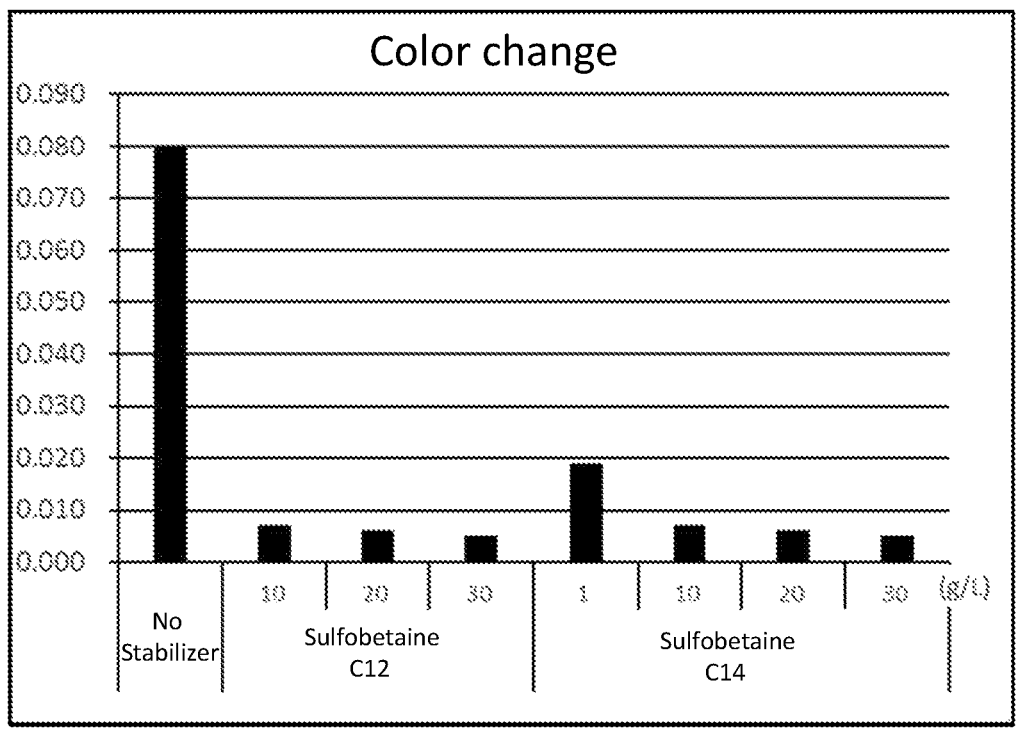
FIG. 2 is a graph showing an evaluation with respect to the concentration dependency of a suppression effect of test compounds on the natural color production of a leuco dye caused by heat treatment.

Table 2 and FIG. 2 show the results.

TABLE 2

|  | Stabilizer | Concentration g/L | Before treatment | After treatment | Difference | Color production ratio |
|---|---|---|---|---|---|---|
| Comp. Ex. 2 | No stabilizer | — | 0.006 | 0.086 | 0.080 | 100 |
| Ex. 6 | Sulfobetaine C12 | 10 | 0.005 | 0.012 | 0.007 | 9 |
| Ex. 7 |  | 20 | 0.005 | 0.011 | 0.006 | 7 |
| Ex. 8 |  | 30 | 0.005 | 0.011 | 0.005 | 7 |
| Ex. 9 | Sulfobetaine C14 | 1 | 0.005 | 0.024 | 0.019 | 24 |
| Ex. 10 |  | 10 | 0.005 | 0.012 | 0.007 | 9 |

TABLE 2-continued

| | Stabilizer | Concentration g/L | Before treatment | After treatment | Difference | Color production ratio |
|---|---|---|---|---|---|---|
| Ex. 11 | | 20 | 0.006 | 0.011 | 0.006 | 7 |
| Ex. 12 | | 30 | 0.007 | 0.012 | 0.005 | 6 |

As shown in FIG. 2 and Table 2, the larger the addition amounts of sulfobetaine C12 and sulfobetaine C14, the further suppressed the color production of the leuco dye was. That is, the leuco dye was stabilized.

Measurement of Hemoglobin A1c (HbA1c) 1

This experiment was performed in order to show that HbA1c % could be measured with high precision using an enzymatic reagent to which a sulfobetaine was added. Hemocyte specimens (37 specimens) derived from diabetic patients were measured using a commercially available measurement reagent and reagents (first reagents and second reagents below) containing the stabilizers of Examples 13 to 20, and the applicability of these examples to clinical tests was evaluated by analyzing the correlation between measurement values. Table 3 below shows the results.

The hemoglobin concentration and the hemoglobin A1c concentration were obtained by calculating absorbance ratios of different wavelengths (main measurement wavelength and complementary measurement wavelength) and converting them by using the calibration curve of the absorbance ratio.

<Sample>
Hemocyte specimens derived from diabetic patients (37 specimens)
<Calibration Sample>
Commercially available HbA1c calibrator (manufactured by ARKRAY Inc.)
<First Reagent>
Horseradish peroxidase: 15 U/mL
Fructosyl peptide oxidase (product name: FPO-302; manufactured by TOYOBO Co., Ltd.): 3 U/mL
Sulfobetaine that is the same as that in the second reagent (various kinds): 3 g/L
PIPES buffer (pH 6.4)
<Second Reagent>
Protease (product name: NEP-209; manufactured by TOYOBO Co., Ltd.): 2 U/mL
DA-67: 45 µmol/L
Sulfobetaine C12/C14 (at the concentration shown in Table 3 below)
PIPES buffer (pH 6.8)
<Measurement Method 1: Hemoglobin Concentration>
Main measurement wavelength: 596 nm
Complementary measurement wavelength: 694 nm
Specimen dispensing amount: 8 µL
First reagent dispensing amount: 96 µL
Second reagent dispensing amount: 24 µL
First photometric point: 17 to 19
<Measurement Method 2: Hemoglobin A1c Concentration>
Main measurement wavelength: 658 nm
Complementary measurement wavelength: 694 nm
Specimen dispensing amount: 8 µL
First reagent dispensing amount: 96 µL
Second reagent dispensing amount: 24 µL
First photometric point: 21
Second photometric point: 40 to 42
<Measurement Method 3: Calculation of HbA1c Value (NGSP)>
The hemoglobin concentration measured in measurement method 1 and the hemoglobin A1c concentration measured in measurement method 2 were taken as $CH_b$ and $CH_{bA1c}$, respectively, and the HbA1c value was calculated using the following equation:

$$HbA1c = CH_{bA1c}/CH_b \times 0.915 \times 100 + 2.15.$$

TABLE 3

| | | Concentration g/L | Content ratio | Gradient | Y intercept | Contribution ratio |
|---|---|---|---|---|---|---|
| Ex. 13 | Sulfobetaine C12 | 1 | 66 | 0.981 | −0.045 | 0.993 |
| Ex. 14 | | 10 | 662 | 1.013 | −0.267 | 0.981 |
| Ex. 15 | | 20 | 1325 | 1.023 | −0.353 | 0.981 |
| Ex. 16 | | 30 | 1987 | 1.015 | −0.250 | 0.985 |
| Ex. 17 | Sulfobetaine C14 | 1 | 61 | 1.001 | −0.141 | 0.988 |
| Ex. 18 | | 10 | 611 | 1.016 | −0.256 | 0.991 |
| Ex. 19 | | 20 | 1222 | 1.032 | −0.235 | 0.995 |
| Ex. 20 | | 30 | 1834 | 1.052 | −0.303 | 0.993 |

*Content ratio: molar ratio, the amount of substance of sulfobetaine/amount of substance of leuco dye As shown in Table 3, when the same specimens (37 specimens) were used to analyze the correlations between the HbA1c values measured using the commercially available measurement kit and the HbA1c values measured when the stabilizers of Examples 13 to 20 were added, favorable correlations were shown as a result.

Measurement of Hemoglobin A1c (HbA1c) 2

This experiment was performed in order to show that measurement performance similar to that as described above was obtained using a reagent having a configuration different from that as described above. As a result, it was confirmed that a reagent having the configuration below performed similarly to the reagent having the configuration above.

<Calibration Sample>
Commercially available HbA1c calibrator (manufactured by ARKRAY Inc.)
<First Reagent>
DA-67: 10 µmol/L
Protease (product name: NEP-209; manufactured by TOYOBO Co., Ltd.): 8 U/mL
Sulfobetaine (C12 or C14): 30 g/L
PIPES buffer (pH 6.8)

<Second Reagent>
Horseradish peroxidase: 60 U/mL
Fructosyl peptide oxidase (product name: FPO-302; manufactured by TOYOBO Co., Ltd.): 12 U/mL
PIPES buffer (pH 6.4)
<Measurement Method 1: Hemoglobin Concentration>
Main measurement wavelength: 596 nm
Complementary measurement wavelength: 694 nm
Specimen dispensing amount: 8 μL
First reagent dispensing amount: 96 μL
Second reagent dispensing amount: 24 μL
First photometric point: 17 to 19
<Measurement Method 2: Hemoglobin A1c Concentration>
Main measurement wavelength: 658 nm
Complementary measurement wavelength: 694 nm
Specimen dispensing amount: 8 μL
First reagent dispensing amount: 96 μL
Second reagent dispensing amount: 24 μL
First photometric point: 21
Second photometric point: 40 to 42
<Measurement Method 3: Calculation of HbA1c Value (NGSP)>

The hemoglobin concentration measured in measurement method 1 and the hemoglobin A1c concentration measured in measurement method 2 were taken as $CH_b$ and $CH_{bA1c}$, respectively, and the HbA1c value was calculated using the following equation:

$$HbA1c = CH_{bA1c}/CH_b \times 0.915 \times 100 + 2.15.$$

Evaluation of Hemoglobin Denaturing Ability and Protease Reaction Promoting Ability of Sulfobetaine When HbA1c % is measured using a reagent for an enzymatic method, it is preferable that hemoglobin is appropriately denatured in order to accurately quantify hemoglobin and promote hydrolysis by using a protease. Therefore, this experiment was performed in order to evaluate the Hb denaturing ability and protease reaction promoting ability of sulfobetaines C12 and C14 under the conditions below.

Figure 3:
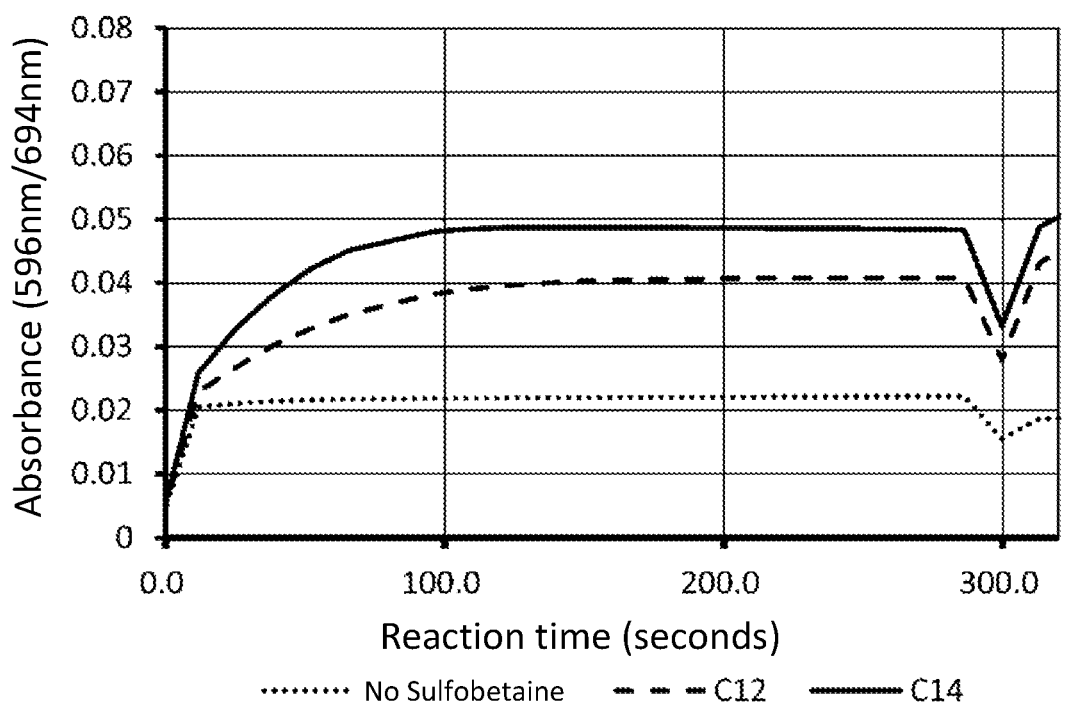
FIG. 3 is a graph showing an evaluation with respect to the hemoglobin denaturing ability of test compounds.
Figure 4:
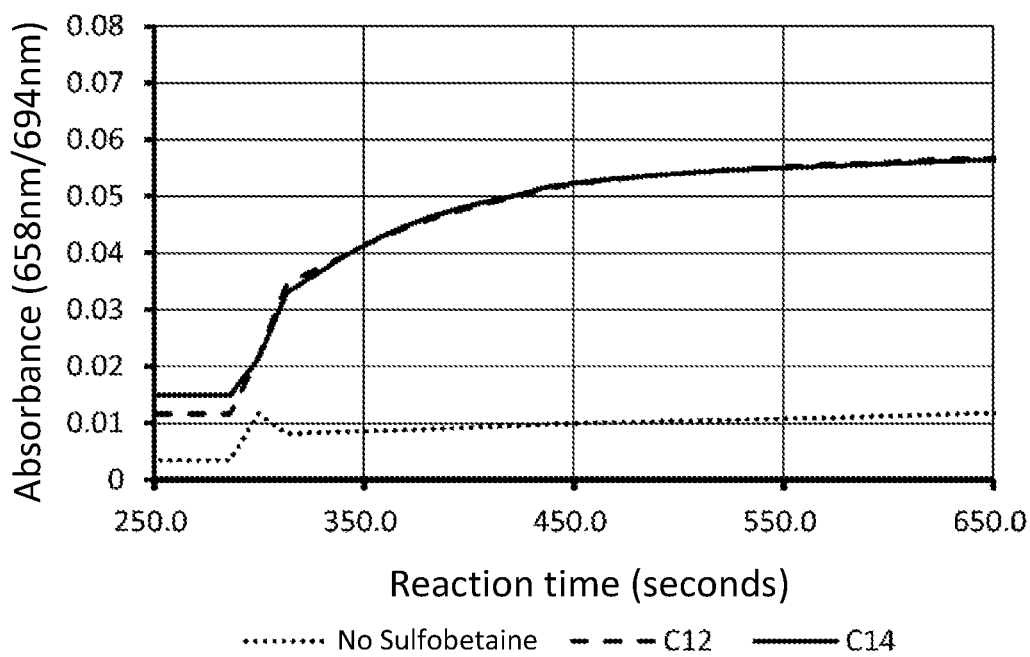
FIG. 4 is a graph showing an evaluation with respect to the protease reaction promoting ability of test compounds.

<Method for Evaluating Hemoglobin Denaturing Ability>
A biological autoanalyzer (JCA-BM-6010, manufactured by JEOL Ltd.) was used to observe the change in the absorbance of hemoglobin for 5 minutes from when a specimen was dispensed until the second reagent was dispensed. FIG. 3 shows the measurement results.
<Measurement Parameters>
Main measurement wavelength: 596 nm
Complementary measurement wavelength: 694 nm
Specimen dispensing amount: 8 μL
First reagent dispensing amount: 96 μL
Second reagent dispensing amount: 24 μL
<Sample>
Specimen obtained by diluting whole blood from a healthy person with purified water by a factor of 23.
<First Reagent>
Horseradish peroxidase: 15 U/mL
Fructosyl peptide oxidase (product name: FPO-302; manufactured by TOYOBO Co., Ltd.): 3 U/mL
Sulfobetaine (C12 or 14): 3 g/L
PIPES buffer: 50 mmol/L (pH 6.4)
<Second Reagent>
Protease (product name: NEP-209; manufactured by TOYOBO Co., Ltd.): 2 U/mL
DA-67: 45 μmol/L
Sulfobetaine that is the same as that in the first reagent: 3 g/L
PIPES buffer: 100 mmol/L (pH 6.8)
<Method for Evaluating Protease Reaction Promoting Ability>
A biological autoanalyzer (JCA-BM-6010, manufactured by JEOL Ltd.) and a measurement reagent whose rate-limiting factor is a protease were used to observe the change in the absorbance of a color forming agent from when a specimen was dispensed until the second reagent was dispensed. FIG. 4 shows the measurement results.
<Measurement Parameters>
Main measurement wavelength: 658 nm
Complementary measurement wavelength: 694 nm
Specimen dispensing amount: 8 μL
First reagent dispensing amount: 96 μL
Second reagent dispensing amount: 24 μL
<Sample>
Specimen obtained by diluting whole blood from a healthy person with purified water by a factor of 23.
<First Reagent>
Horseradish peroxidase: 15 U/mL
Fructosyl peptide oxidase (product name: FPO-302; manufactured by TOYOBO Co., Ltd.): 3 U/mL
Sulfobetaine (C12/C14): 3 g/L
PIPES buffer: 50 mmol/L (pH 6.4)
<Second Reagent>
Protease (product name: NEP-209; manufactured by TOYOBO Co., Ltd.): 2 U/mL
DA-67: 45 μmol/L
Sulfobetaine that is the same as that in the first reagent: 3 g/L
PIPES buffer: 100 mmol/L (pH 6.8)

As shown in FIGS. 3 and 4, the sulfobetaines C12 and C14 had a Hb denaturing ability and a protease reaction promoting ability.

The invention may be embodied in other forms without departing from the spirit or essential characteristics thereof. The embodiments disclosed in this application are to be considered in all respects as illustrative and not limiting. The scope of the invention is indicated by the appended claims rather than by the foregoing description, and all changes which come within the meaning and range of equivalency of the claims are intended to be embraced therein.

The invention claimed is:

1. A reagent for measuring a glycoprotein, comprising a leuco dye; and
a compound represented by Formula (I):

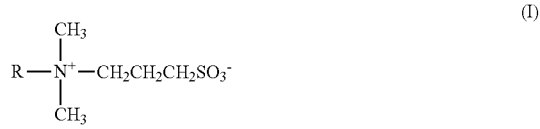

where R represents a hydrocarbon chain having 8 to 17 carbon atoms.

2. The reagent according to claim 1, wherein the glycoprotein is glycohemoglobin or glycoalbumin.

3. The reagent according to claim 1, wherein the glycoprotein is hemoglobin A1c.

4. The reagent according to claim 1, wherein the compound represented by Formula (I) is included in the reagent as at least an agent for stabilizing the leuco dye.

5. The reagent according to claim 1, wherein the leuco dye is 10-(carboxymethylaminocarbonyl)-3,7-bis(dimethylamino)phenothiazine, N,N,N',N',N'',N''-hexa(3-sulfopropyl)-4,4',4"-triaminotriphenylmethane, N-(carboxymethyl-aminocarbonyl)-4,4'-bis(dimethylamino)diphenylamine, or a salt thereof.

6. A kit for measuring a glycoprotein, comprising:
a second reagent containing a peroxidase; and
the reagent according to claim 1.

7. A method for measuring hemoglobin A1c comprising,
mixing a sample and the reagent according to claim 1, wherein the mixing comprises denaturing hemoglobin in the sample;
reacting glycohemoglobin in the sample with a protease to produce an N-terminal glycated peptide;
reacting the N-terminal glycated peptide with a fructosyl peptide oxidase to produce hydrogen peroxide;
reacting the produced hydrogen peroxide with a peroxidase to allow the leuco dye to produce a color; and
measuring the developed color signals, and calculating a hemoglobin A1c level and a hemoglobin level.

8. A method for measuring hemoglobin A1c comprising,
mixing a sample and the reagent according to claim 1, wherein the mixing comprises denaturing hemoglobin in the sample;
reacting glycohemoglobin in the sample with a glycoprotein-directed fructosyl peptide oxidase to produce hydrogen peroxide;
reacting the produced hydrogen peroxide with a peroxidase to allow the leuco dye to produce a color; and
measuring the developed color signals, and calculating a hemoglobin A1c level and a hemoglobin level.

9. The reagent according to claim 1, wherein the compound represented by Formula (I) is N-octyl-N,N-dimethyl-3-ammonio-1-propanesulfonic acid.

10. The reagent according to claim 1, wherein the compound represented by Formula (I) is N-decyl-N,N-dimethyl-3-ammonio-1-propanesulfonic acid.

11. The reagent according to claim 1, wherein the compound represented by Formula (I) is N-dodecyl-N,N-dimethyl-3-ammonio-1-propanesulfonic acid.

12. The reagent according to claim 1, wherein the compound represented by Formula (I) is N-tetradecyl-N,N-dimethyl-3-ammonio-1-propanesulfonic acid, and N-hexadecyl-N,N-dimethyl-3-ammonio-1-propanesulfonic acid.

13. The reagent according to claim 1, wherein the compound represented by Formula (I) is N-hexadecyl-N,N-dimethyl-3-ammonio-1-propanesulfonic acid.

* * * * *